US00PP27546P3

(12) United States Plant Patent
Kolster

(10) Patent No.: US PP27,546 P3
(45) Date of Patent: Jan. 17, 2017

(54) ***EXOCHORDA* PLANT NAMED 'KOLMAGISNO'**

(50) Latin Name: ***Exochorda* hybrid**
Varietal Denomination: Kolmagisno

(71) Applicant: Kolster HOlding BV, Boskoop (NL)

(72) Inventor: Peter R. Kolster, Boskoop (NL)

(73) Assignee: KOLSTER HOLDING BV, Boskoop (NL)

( * ) Notice: Subject to any disclaimer, the term of this patent is extended or adjusted under 35 U.S.C. 154(b) by 63 days.

(21) Appl. No.: 14/545,493

(22) Filed: May 12, 2015

(65) Prior Publication Data

US 2016/0174444 P1 Jun. 16, 2016

(30) Foreign Application Priority Data

Dec. 12, 2014 (QZ) ..... PBR 2014/3392

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

UPOV hit on 'Kolmagisno', QZ PBR 20143392, published Feb. 15, 2015.*

* cited by examiner

*Primary Examiner* — Anne Grunberg
(74) *Attorney, Agent, or Firm* — Penny J. Aguirre

(57) ABSTRACT

A new cultivar of *Exochorda* plant named, 'Kolmagisno', that is characterized by its well-branched, upright, and compact plant habit, its flowers that are bright white in color, and its floriferous blooming habit.

2 Drawing Sheets

Botanical classification: *Exochorda* hybrid.
Variety denomination: 'Kolmagisno'.

BACKGROUND OF THE INVENTION

The present invention relates to a new and distinct cultivar of *Exochorda* of hybrid origin. The new cultivar will be referred to hereafter by its cultivar name, 'Kolmagisno'. 'Kolmagisno' is a new cultivar of deciduous shrub grown for use as a landscape shrub.

The new cultivar is a selection from a controlled breeding program conducted by the Inventor at his nursery in Boskoop, The Netherlands with the goal of selecting new cultivars of *Exochorda* that are floriferous with upright plant habits.

'Kolmagisno' was derived from a cross made in by the Inventor in March of 2006 between an unnamed plant of *Exochorda serratifolia* (not patented) as the female parent and *Exochorda macrantha* 'The Bride' (not patented) as the male parent. 'Kolmagisno' was selected in 2011 as a single unique plant amongst the resulting seedlings.

Asexual propagation of the new cultivar was first accomplished by the Inventor via stem cuttings in Boskoop, The Netherlands in June of 2011. Asexual propagation by stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Kolmagisno' as a unique cultivar of *Exochorda*.

1. 'Kolmagisno' exhibits a well branched, upright, and compact plant habit.
2. 'Kolmagisno' exhibits flowers that are bright white in color.
3. 'Kolmagisno' exhibits a floriferous blooming habit.

The female parent of 'Kolmagisno' differs from 'Kolmagisno' in having a much less compact plant habit and in being less floriferous. The male parent of 'Kolmagisno', 'The Bride', differs from 'Kolmagisno' in having a mounded plant habit with arching branches. 'Kolmagisno' can also be compared to the *Exochorda* cultivars 'Niagara' (U.S. Plant Pat. No. 21,665) and 'Snow White' (not patented). 'Niagara' is similar to 'Kolmagisno' in having an upright plant habit. 'Niagara' differs from 'Kolmagisno' in having a less compact plant habit and in being less well branched. 'Snow White' is similar to 'Kolmagisno' in having a moderate growth rate. 'Snow White' differs from 'Kolmagisno' in having a larger plant size and in having a bloom period that commences earlier.

BRIEF DESCRIPTION OF THE DRAWINGS

The accompanying colored photographs illustrate the overall appearance and distinct characteristics of the new cultivar. The photographs were taken of a five year-old plant of the new cultivar as grown outdoors in a 10-liter container in Boskoop, The Netherlands.

The photograph in FIG. 1 provides a side-view of a plant of 'Kolmagisno' in bloom.

Figure 1:
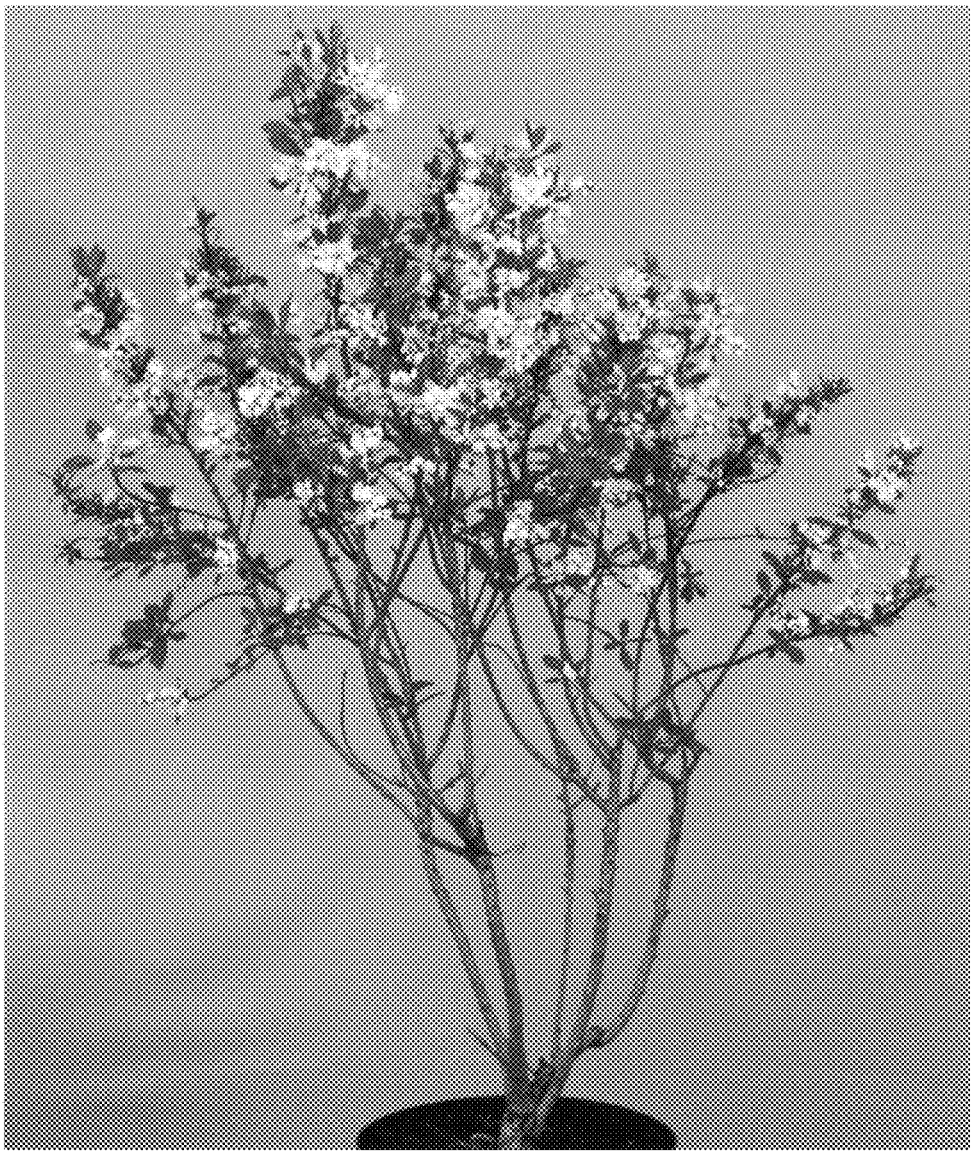
Figure 2:
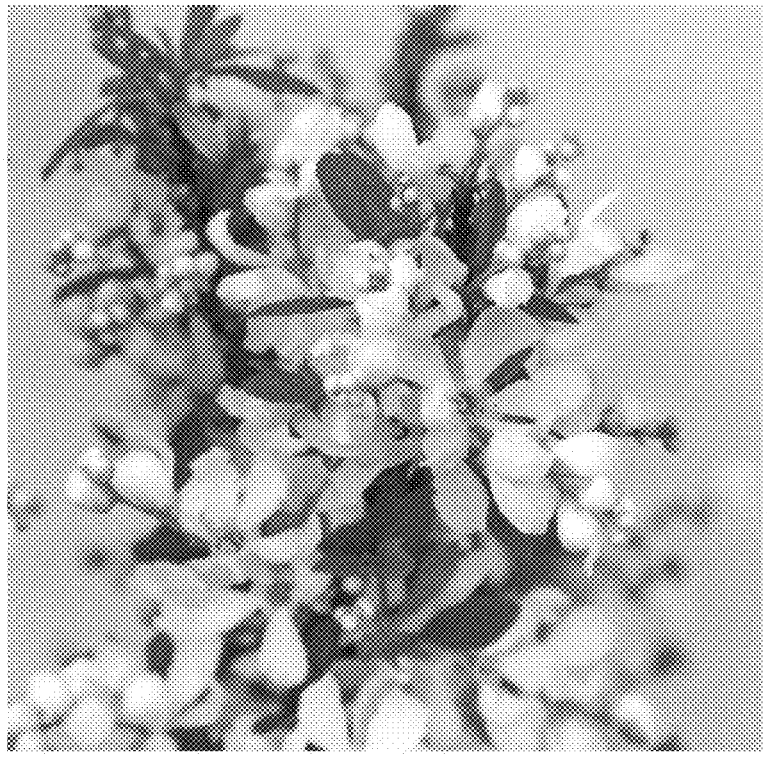

The photograph in FIG. 2 provides a close-up view of inflorescences of 'Kolmagisno'.

Figure 3:
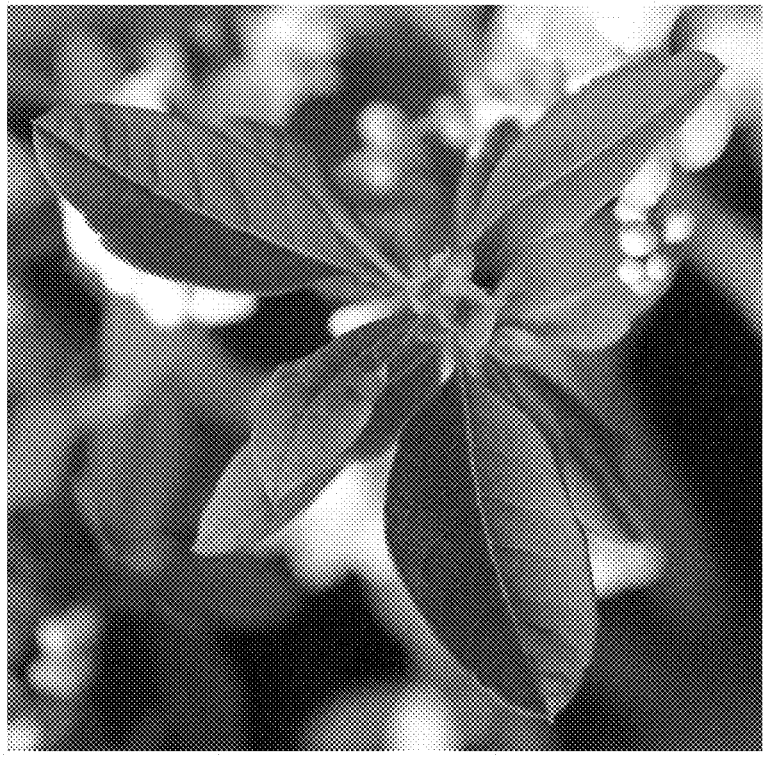

The photograph in FIG. 3 provides a close-up view of the foliage of 'Kolmagisno'.

The colors in the photographs are as close as possible with the photographic and printing technology utilized and the color values cited in the Detailed Botanical Description accurately describe the colors of the new *Exochorda*.

DETAILED BOTANICAL DESCRIPTION

The following is a detailed description of five year-old plants of the new cultivar as grown in 10-liter containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from April to early May in The Netherlands.

*Plant type*.—Perennial shrub.

*Plant habit*.—Upright and compact.

*Height and spread*.—An average of 1 m in height and 60 cm in spread.

*Cold hardiness*.—At least to U.S.D.A. Zone 5.

*Diseases*.—No susceptibility or resistance to diseases has been observed.

*Propagation*.—Stem cuttings.

*Growth rate*.—Moderate.

*Roots*.—Fleshy when young; becoming fibrous on mature plants.

Branch description:

*Stem color*.—Young; 144B, mature; N199C.

*Stem shape*.—Rounded.

*Stem strength*.—Moderately strong.

*Stem surface*.—Glabrous, moderately glossy.

*Branching*.—Freely branching with an average of 59 lateral branches.

*Stem size*.—An average of 27.4 cm in length and 3 mm in diameter.

Foliage description:

*Leaves*.—Simple, elliptic-oblong to obovate in shape, alternate arrangement, an average of 5.1 cm in length and 2.4 cm in width, abruptly acute apex, attenuate base, margin; entire and occasionally very slightly serrate near the top, internode length is an average of 1.5 cm, attachment petiolate, color; new growth upper surface; 143A and lower surface; 143C, mature upper surface; 137A to 137B and lower surface; 138B, venation; pinnate, vein color; upper surface 144B, lower surface 145B , upper and lower surfaces; glabrous and dull, bud-scales; present at the base of emerging leaves, 47D in color, not persistent.

*Petioles*.—An average of 1.4 cm in length and 1 mm in diameter, 145B in color, smooth surface.

Inflorescence description:

*Inflorescence type*.—Raceme.

*Inflorescence size*.—An average of 7 cm in height and 4 cm in diameter.

*Inflorescence number*.—An average of 42 per plant.

*Flower number*.—An average of 11 flowers per inflorescence.

*Flower fragrance*.—None.

*Flower longevity*.—About 12 days, self-cleaning.

*Flower type*.—Single, rotate.

*Flower size*.—An average of 3.7 cm in diameter and 1.3 cm in depth.

*Flower aspect*.—Upright to outward.

*Peduncles*.—An average of 6.5 cm in length and 1 mm in diameter, terminal peduncles held at an average angle of 0°, straight on top of lateral branch, axillary peduncles held in an average angle of 50° to lateral branches, moderate in strength, 144B in color, surface is smooth.

*Pedicels*.—An average of 2 mm in length and 0.75 mm in diameter, held at an average angle of 45° to peduncle, moderate in strength, 144B in color, surface is smooth.

*Flower buds*.—Flattened globular in shape, an average of 5 mm in length and 6 mm in diameter, color; lower half 145C and upper half NN155D.

*Petals*.—5, broad obovate to spathulate shape, upper and lower surfaces are moderately glossy, slightly crinkled and glabrous, entire margin, cuneate base, obtuse to broadly retuse apex, an average of 1.7 cm in length and 1 cm width, color: when opening and when fully open upper and lower surface; NN155D, color not fading.

*Sepals*.—5, obovate in shape, lower half fused, an average of 4 mm in length and width, fimbriate apex and margin, fused base, upper and lower surfaces glabrous and dull, color: immature upper surface and mature lower surface 150D with proximal half 144A, immature lower surface and mature upper surface 150D with proximal half 147D.

*Calyx*.—Rotate, lower half fused forming a cup-like structure, an average of 3 mm in length and 1 mm in diameter.

Reproductive organs:

*Pistils*.—5, an average of 1 mm in length, stigma; flattened club-shaped and 151D in color, style; an average of 0.5 mm in length and 151D in color, ovary is 144A in color.

*Stamens*.—An average of 25, in 5 groups of 5, placed at the base of each petal, anther; dorsifixed, broad kidney-shaped, an average of 0.75 mm in length and 161D in color, filament; an average of 2 mm in length and 157D in color, pollen is low in quantity and 160D in color.

*Fruit*.—No fruit or seed production has been observed.

It is claimed:

1. A new and distinct cultivar *Exochorda* plant named 'Kolmagisno' as herein illustrated and described.

* * * * *